(12) United States Patent
Hadba et al.

(10) Patent No.: US 12,396,843 B2
(45) Date of Patent: *Aug. 26, 2025

(54) HEAT TUNABLE INTRAOCULAR LENS

(71) Applicant: Alcon Inc., Fribourg (CH)

(72) Inventors: Ahmad Hadba, Fort Worth, TX (US); Ramiro Ribeiro, Arlington, MA (US); Douglas Schlueter, Azle, TX (US); Marcel Ackermann, Enschede (NL); Lukas Scheibler, Telluride, CO (US); Stefan Troller, Sissach (CH)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/306,347

(22) Filed: Apr. 25, 2023

(65) Prior Publication Data

US 2023/0255751 A1    Aug. 17, 2023

Related U.S. Application Data

(60) Continuation of application No. 16/861,379, filed on Apr. 29, 2020, now Pat. No. 11,666,432, which is a (Continued)

(51) Int. Cl.
*A61F 2/16* (2006.01)

(52) U.S. Cl.
CPC .......... *A61F 2/1659* (2013.01); *A61F 2/1613* (2013.01); *A61F 2/1618* (2013.01); (Continued)

(58) Field of Classification Search
CPC .... A61F 2/1613; A61F 2/1627; A61F 2/1635; A61F 2250/0003; A61F 2/1659; A61F 2210/0014; A61F 2210/0047
See application file for complete search history.

(56) References Cited

U.S. PATENT DOCUMENTS

| 4,575,373 A | 3/1986 | Johnson |
|---|---|---|
| 2003/0060878 A1 | 3/2003 | Shadduck |

(Continued)

FOREIGN PATENT DOCUMENTS

| JP | 2006-506196 | 2/2006 |
|---|---|---|
| JP | 2006-515189 | 5/2006 |

(Continued)

OTHER PUBLICATIONS

U.S. Appl. No. 16/861,379, filed Apr. 29, 2020.
U.S. Appl. No. 16/189,115, filed Nov. 13, 2018.
U.S. Appl. No. 15/275,625, filed Sep. 26, 2016.

*Primary Examiner* — Javier G Blanco
(74) *Attorney, Agent, or Firm* — Levine Bagade Han LLP

(57) ABSTRACT

A method and system provide an ophthalmic lens including a lens body having a chamber therein, a reservoir module coupled with the lens body and an optical fluid. At least part of the lens body is flexible. The reservoir module includes a reservoir and a heat sensitive portion bordering the reservoir. The reservoir has a reservoir volume and is fluidically connected with the chamber. The heat sensitive portion has a shape responsive to a temperature of at least forty five degrees Celsius such that the reservoir volume changes in response to at least part of the heat sensitive portion reaching the temperature. The optical fluid resides in the chamber and the reservoir. A change in the reservoir volume flows a portion of the optical fluid between the reservoir and the chamber such that the flexible portion of the lens body undergoes a shape change corresponding to a base power change.

12 Claims, 5 Drawing Sheets

Related U.S. Application Data continuation of application No. 16/189,115, filed on Nov. 13, 2018, now Pat. No. 10,786,348, which is a division of application No. 15/275,625, filed on Sep. 26, 2016, now Pat. No. 10,159,566.

(52) U.S. Cl.
CPC .......... *A61F 2/1635* (2013.01); *A61F 2/1627* (2013.01); *A61F 2002/169* (2015.04); *A61F 2210/0014* (2013.01); *A61F 2210/0047* (2013.01); *A61F 2210/0061* (2013.01); *A61F 2230/0065* (2013.01); *A61F 2250/0003* (2013.01); *A61F 2250/0009* (2013.01)

(56) References Cited

U.S. PATENT DOCUMENTS

| | | |
|---|---|---|
| 2003/0147046 A1 | 8/2003 | Shadduck |
| 2004/0169932 A1 | 9/2004 | Esch et al. |
| 2007/0299487 A1 | 12/2007 | Shadduck |
| 2016/0058553 A1 | 3/2016 | Salahieh |

FOREIGN PATENT DOCUMENTS

| | | |
|---|---|---|
| JP | 2006515489 A | 5/2006 |
| JP | 2006-517447 | 7/2006 |
| JP | 2006523130 A | 10/2006 |
| KR | 1020110133618 | 12/2011 |
| KR | 1020160010428 | 1/2016 |
| WO | WO 2004/046768 | 6/2004 |
| WO | 2004068750 A1 | 8/2004 |
| WO | 2004081613 A2 | 9/2004 |
| WO | WO 2009/015234 | 1/2009 |
| WO | WO 2018/055477 | 3/2018 |

HEAT TUNABLE INTRAOCULAR LENS

PRIORITY CLAIM

This application is a continuation of U.S. Continuation application Ser. No. 16/861,379 filed on Apr. 29, 2020, which is a continuation of U.S. Divisional application Ser. No. 16/189,115, which claims the benefit of priority of U.S. Non-Provisional patent application Ser. No. 15/275,625 titled "Heat Tunable Intraocular Lens," filed on Sep. 26 2016, whose inventors are Ramiro Ribeiro, Douglas Schlueter, Lukas Scheibler, Ahmad R. Hadba, Stefan Troller and Marcel Ackermann, which is hereby incorporated by reference in its entirety as though fully and completely set forth herein.

FIELD

The present disclosure relates generally ophthalmic lenses and, more particularly, to a heat tunable intraocular lens.

BACKGROUND

Intraocular lenses (IOLs) are implanted in patients' eyes either to replace a patient's lens or, in the case of a phakic IOL, to complement the patient's lens. Some conventional IOLs are single focal length IOLs, while others are multifocal IOLs. Single focal length IOLs have a single focal length or single power. Objects at the focal length from the eye/IOL are in focus, while objects nearer or further away may be out of focus. Multifocal IOLs, on the other hand, have at least two focal lengths. Multifocal lenses may assist patients having conditions such as near-sightedness. In general, a physician selects an IOL having the appropriate base power and other characteristics for the patient. During ophthalmic surgery, often performed for other conditions such as cataracts, the selected IOL is implanted.

Although the IOLs function acceptably well in most patients, the selected IOL may have incorrect power for the patient. The IOL can be removed and a new IOL selected and implanted. However, performing additional ophthalmic surgeries for this purpose is undesirable. Other IOLs may have their power adjusted noninvasively. For example, the IOL may be sensitive to ultraviolet (UV) light. Such an IOL may be exposed to UV light in order to change the power of the lens. The exposure to UV light may change the shape of the IOL and, therefore, the base power of the lens. Although this method allows the base power of the IOL to be adjusted, such an IOL requires the patient to wear UV light blocking glasses at all times until an adjustment phase is completed. The adjustment phase is typically on the order of two weeks. Requiring a patient to wear UV light blocking glasses twenty-four hours per day for two weeks is inconvenient for the patient and undesirable. Once the adjustment phase is completed, the changes to the IOL must be locked in to prevent further changes to the IOL power due to every day exposure to UV light. Once these changes are locked in, no further adjustments may be made to the base power of the IOL. Other mechanisms, such as a change in tension, exist to change the base power of the lens. However, these mechanisms have attendant issues shortcomings.

Accordingly, what is needed is an improved mechanism for noninvasively changing the base power of an IOL.

BRIEF SUMMARY OF THE INVENTION

A method and system provide an ophthalmic lens including a lens body having a chamber therein, a reservoir module coupled with the lens body and an optical fluid. At least a portion of the lens body is flexible. The reservoir module includes a heat sensitive portion and has a reservoir therein. The reservoir has a reservoir volume and is fluidically connected with the chamber. The heat sensitive portion of the reservoir module borders at least a portion of the reservoir. The heat sensitive portion has a shape responsive to a temperature of at least forty five degrees Celsius such that the reservoir volume changes in response to at least part of the heat sensitive portion reaching the temperature. The optical fluid resides in the chamber and the reservoir. The optical fluid has an optical fluid index of refraction that matches the lens body index of refraction to within 0.1. A change in the reservoir volume flows a portion of the optical fluid between the reservoir and the chamber such that the at least the portion of the lens body undergoes a shape change corresponding to a base power change.

According to the method and system disclosed herein, a physician may be better and more easily able to noninvasively change the power of an implanted ophthalmic device such as an IOL.

BRIEF DESCRIPTION OF SEVERAL VIEWS OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION OF THE PREFERRED EMBODIMENTS

The exemplary embodiments relate to ophthalmic devices such as intraocular lenses (IOLs). The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein. The method and system are also described in terms of singular items rather than plural items. One of ordinary skill in the art will recognize that these singular terms encompass plural. For example, a chamber may include one or more chambers.

A method and system provide an ophthalmic lens including a lens body having a chamber therein, a reservoir module coupled with the lens body and an optical fluid. At least a portion of the lens body is flexible. The reservoir module includes a heat sensitive portion and has a reservoir therein. The reservoir has a reservoir volume and is fluidically connected with the chamber. The heat sensitive portion of the reservoir module borders at least a portion of the reservoir. The heat sensitive portion has a shape responsive to a temperature of at least forty five degrees Celsius such that the reservoir volume changes in response to at least part of the heat sensitive portion reaching the temperature. The optical fluid resides in the chamber and the reservoir. The optical fluid has an optical fluid index of refraction that matches the lens body index of refraction to within 0.1. A change in the reservoir volume flows a portion of the optical fluid between the reservoir and the chamber such that the at least the portion of the lens body undergoes a shape change corresponding to a base power change.

Figure 1A:
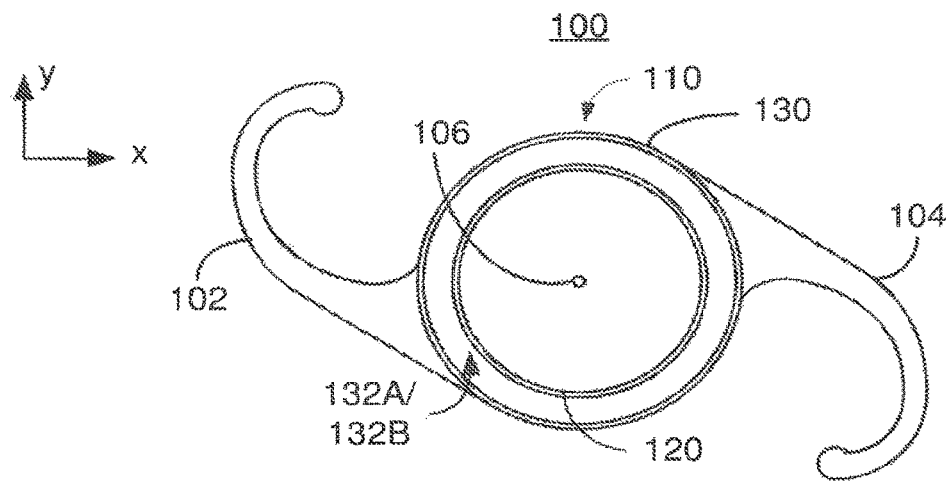
FIGS. 1A-1E depict various views of an exemplary embodiment of a heat tunable ophthalmic device.

FIGS. 1A-1E depict an exemplary embodiment of a heat tunable ophthalmic device 100 that may be used as an IOL. For simplicity, the ophthalmic device 100 is referred to hereinafter as an IOL 100. FIG. 1A depicts a plan view of the IOL 100, while FIGS. 1B-1E depicts side views of the ophthalmic lens 110. For clarity, FIGS. 1A-1E are not to scale. The IOL 100 includes an ophthalmic lens 110 as well as haptics 102 and 104. Portions of the ophthalmic lens 110 may include a variety of optical materials including but not limited to one or more of silicone, a hydrogel and an acrylic. Haptics 102 and 104 are used to hold the ophthalmic device 100 in place in a patient's eye (not explicitly shown). However, in other embodiments, other mechanism(s) might be used to retain the ophthalmic device in position in the eye. For clarity, the haptics are not depicted in FIGS. 1B-3C, discussed below. Although the ophthalmic lens 110 is depicted as having a circular cross section in the plan view of FIG. 1A, in other embodiments, other shapes may be used.

The ophthalmic lens 110 (hereinafter "lens") has an optic axis 106 as well a lens body 120, a reservoir module 130 and optical fluid 140. Although termed part of the lens 110, the optic axis 106 may be considered an imaginary line that passes through the centers of the anterior surface and posterior surface. Thus, the optic axis 106 is shown as a dashed line. The optic axis 106 may also be perpendicular to the surfaces and at the point at which it passes through the surfaces. Although not shown, the anterior and/or posterior surface may have other features included but not limited to diffraction grating(s). Although indicated as separate components, the reservoir module 130 and the lens body 120 may be integrated together into a single piece. For example, some or all of the lens body 120 and reservoir module may be a monolithic structure formed together.

The lens body 120 forms the primary optical component of the IOL 100. Thus, light passes through the lens body 120 and other components of the eye, allowing the patient to see. In some embodiments, the reservoir module 130 is not designed to transmit light used in vision. The lens body 120 includes a base 122, a flexible portion 124 and a chamber 126. In the embodiment shown, the flexible portion 124 is considered to be a flexible membrane 124. Consequently, the flexible portion 124 is referred to hereinafter as a flexible membrane 124. However, nothing prevents the flexible portion from having another configuration. The chamber 126 may be considered to be the space between the base 122 and the flexible membrane 124. An optical fluid 140, discussed below, resides in at least the chamber 126.

In the embodiment shown, the base 122 has stable optical properties. Thus, the base 122 may be relatively fixed in shape. In other embodiments, the base 122 may change shape somewhat in response to changes in the volume of the chamber 126. In contrast, the flexible membrane 124 is flexible and changes shape in response to a change in volume of the reservoir 126.

In some embodiments, the base 122 and flexible membrane 124 may be made of the same material, such as AcrySof®, AcrySof® 2 and/or other soft optical material(s) might be used. In other embodiments, the base 122 and the flexible membrane 124 may be made of different materials. The base 122 may be sufficiently thick that the shape of the base 122 remains substantially unchanged. However, the flexible membrane 124 is sufficiently thin to respond to changes to the volume of the chamber 126. For example, the flexible membrane 124 may be at least eighty micrometers thick and not more than three hundred micrometers thick. In other embodiments, other thicknesses are possible. In some embodiments, the flexible membrane 124 has a uniform thickness prior to the optical fluid 140 being provided. In other embodiments, the thickness of the flexible membrane 124 may be nonuniform.

Figure 1B:
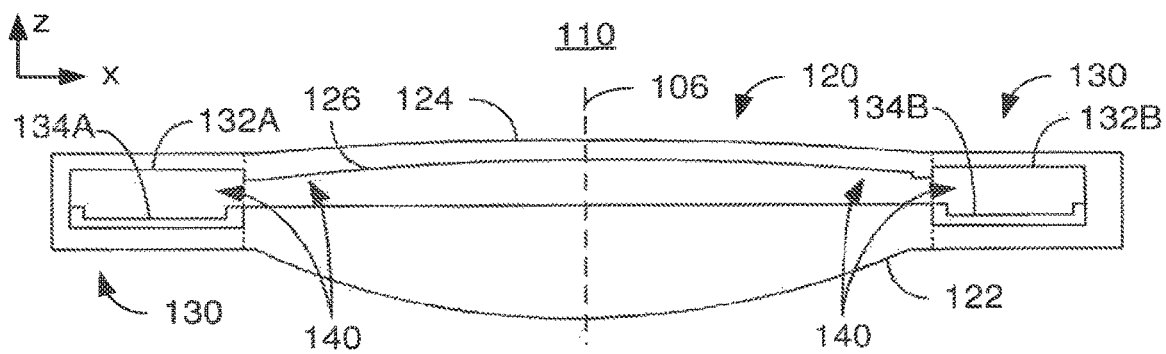
Figure 1C:
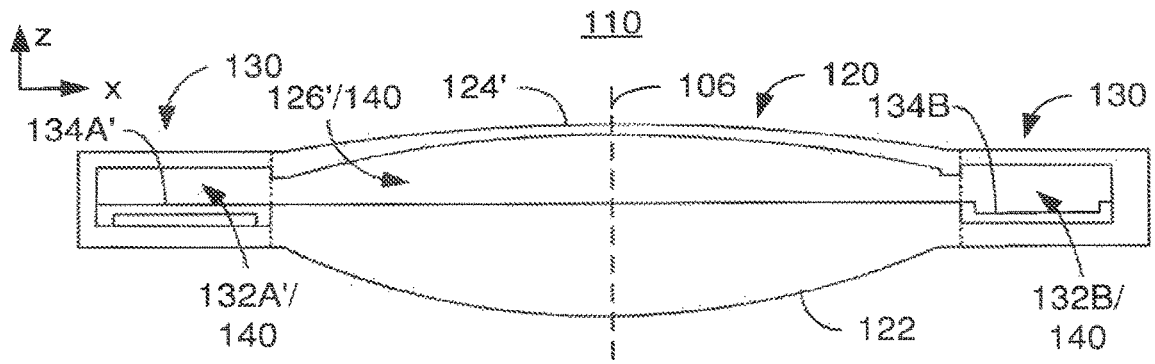
Figure 1D:
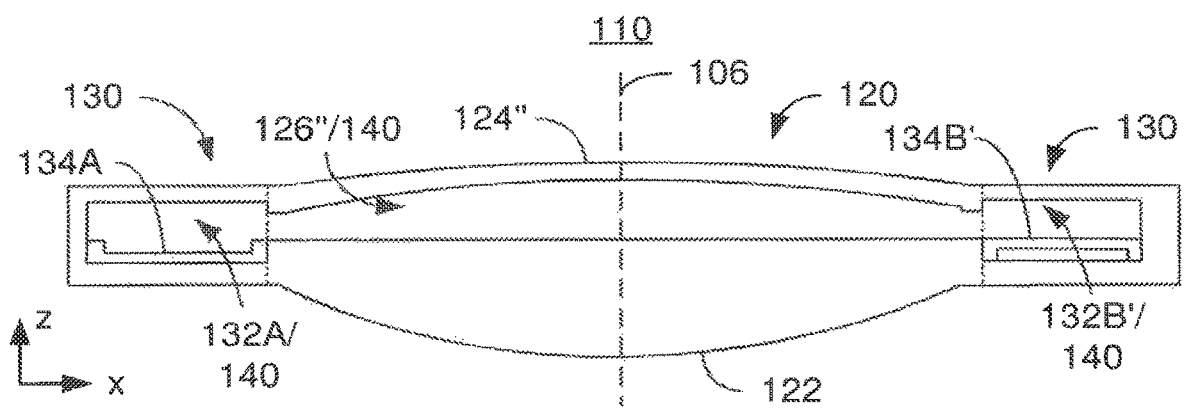

The reservoir module 130 is at the periphery of the lens body 120 and includes reservoir 132A/132B and a heat sensitive portion 134. In FIGS. 1B-1D, cross sections are shown. Thus, the reservoir 132A and reservoir 132B (collectively referred to as reservoir 132A/132B) and the heat sensitive portions 134A and 134B are shown. In some embodiments, the reservoirs 132A and 132B are connected within the reservoir module 130 such that fluid may flow around the periphery of the lens body 120. For example, the reservoirs 132A and 132B may simply be part of a hollow torus (i.e. a tube). In other embodiments, the reservoirs 132A and 132B may be disconnected such that any fluid flow between the reservoirs 132A and 132B occurs through the chamber 126 of the lens body 120. The reservoirs 132A and 132B may have different shape(s) in other embodiments.

The reservoir 132A and 132B are fluidically connected with the chamber 126 of the lens body 120. In the embodiment shown, there are simply inlets/exits (i.e. apertures or channels) between the chamber 126 and the reservoirs 132A and 132B. In other embodiments, the fluid path between the chamber 126 and the reservoir(s) 132A and/or 132B may be more complex.

Figure 1E:
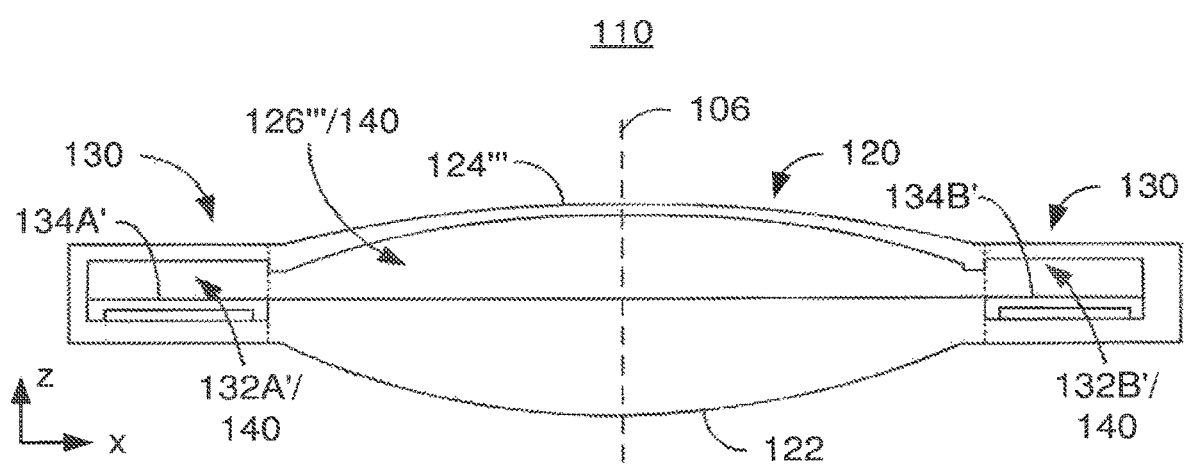

The optical fluid 140 resides in the chamber 126 and reservoir 132A/132B. For simplicity, the optical fluid 140 is only separately labeled in FIG. 1B. In FIGS. 1C-1E, the optical fluid is labeled along with the reservoir 132A/132B and the chamber 126. The optical fluid 140 may flow between the chamber 126 and the reservoir 132A/132B. Because the optical fluid 140 can be in the chamber 126, the optical fluid 140 is in the path of light used for vision. Thus, the optical fluid 140 transmits light. Because light is refracted by the lens body 120, the optical fluid 140 may also have an index of refraction that matches that of the lens body 120 (e.g. at least the base 122 and in some embodiments the base 122 and flexible membrane 124) to within particular limits. For example, in some embodiments, the index of refraction of the optical fluid 140 is within 0.1 of that of the lens body 120. In some embodiments, the index of refraction of the optical fluid 140 is not more than 0.05 different from that of the lens body 120. If the lens body 120 is made of a material such as AcrySof® or AcrySof® 2, the optical fluid 140 may be a high molecular weight aromatic silicone copolymer liquid.

The heat sensitive portions 134A and 134B of the reservoir module 130 may be part of a single heat sensitive portion. For example, the heat sensitive portions 134A and 134B may be part of a torus that occupies one wall of the reservoir 132A/132B. The heat sensitive portions 134A/134B may have different shapes in other embodiments. For example, the heat sensitive portions 134A and/or 134B may be spherical, hemispherical, cubic, elliptical or have other discrete shapes. These shapes may be connected or separate. In addition, the heat sensitive portion 134A may have a different shape than the heat sensitive portion 134B. In the embodiment shown, the heat sensitive portions 134A and 134B have different sizes. However, in other embodiments, the heat sensitive portions 134A and 134B may have the same size.

The heat sensitive portions 134A and 134B change shape in response to a particular temperature (hereinafter, the "glass transition temperature") being reached. In the embodiment shown, the heat sensitive portions 134A and 134B are formed of the same material and have the same glass transition temperature. In other embodiments, the heat sensitive portions 134A and 134B may be formed of different materials and/or have different glass transition temperatures. This glass transition temperature of the heat sensitive portions 134A and 134B is desired to be above the normal temperature of the eye. The glass transition temperature is also desired to be sufficiently low that the heat sensitive portions 134A and 134B may reach the glass transition temperature without damaging the eye. In some embodiments, the heat sensitive portions 134A and 134B are sufficiently small that localized heating of these portions 134A and 134B does not adversely affect the eye even though temperatures well above the normal temperature of the eye are reached by the portions 134A and 134B. For example, the normal temperature of the eye in which the IOL 100 is desired to reside may be approximately thirty-five degrees Celsius through forty degrees Celsius. The glass transition temperature of the heat sensitive portions 134A and 134B may be at least forty five degrees Celsius. In some embodiments, the glass transition temperature may be at least sixty degrees Celsius. In other embodiments, the glass transition temperature may be at least ninety degrees Celsius in some embodiments. In addition, the glass transition temperature may be desired to be less than one hundred degrees Celsius.

At the normal temperature of the eye the shapes of the heat sensitive portions 134A and 134B are constant. If one or both of the heat sensitive portions 134A and 134B are heated to the glass transition temperature, the shape(s) change. Upon cooling, the heat sensitive portion(s) 134A and 134B retain the new shape. This shape then remains constant. Thus, normal wear of the IOL 100 does not affect the base power of the lens 110 or the shape of the heat sensitive portions 134A and 134B. For example, the heat sensitive portions 134A and 134B may be formed of a shape memory material, such as a shape memory polymer (SMP). In addition, the SMP may have an additive (e.g., a dye or other material) added to absorb the light in the wavelength range provided by a laser for heating.

Operation of the IOL 100 may be seen in FIGS. 1B-1E. Initially, as shown in FIG. 1B, the heat sensitive portions 134A and 134B have a particular shape. The heat sensitive portion 134A may be heated to at or above the glass transition temperature. In some embodiments, this heating is accomplished via a laser. For example, a laser may be aimed and fired at the heat sensitive portion 134A. The wavelength of the laser is selected to be transmitted through the cornea and vitreous humor of the eye. In some embodiments, the laser may have a characteristic wavelength of approximately 1064 nm. In other embodiments, the laser may be in the wavelength bandwidth of 750-850 nanometers. The heat sensitive portion 134A heats to at least the glass transition temperature and changes shape.

FIG. 1C depicts the lens 110 after heating of the heat sensitive portion 134A to at least the glass transition temperature. The lens 110 may also have been cooled. The heat sensitive portion 134A' has changed shape. As a result, the volume of the reservoir 132A' has decreased. This forces some of the optical fluid 140 into the chamber 126'. Because the flexible membrane 124' is not rigid, movement of the optical fluid 140 into the chamber 126' increases the volume of the chamber 126' and changes the shape of the flexible membrane 124'. Thus, the power of the lens 110 has been changed. Based on the changes in volume of the reservoir 132A' and chamber 126' and the properties of the flexible membrane 124' and the optical fluid 140, the change in the base power of the lens 110 may be determined.

Alternatively, the heat sensitive portion 134B may be heated to at or above the glass transition temperature. Heating may be accomplished using a laser or similar mechanism in the same manner as describe above. FIG. 1D depicts the lens 110 after heating of the heat sensitive portion 134B. The lens 110 may also have been cooled. The heat sensitive portion 134B' has changed shape. As a result, the volume of the reservoir 132B' has decreased. This forces some of the optical fluid 140 into the chamber 126". Because the flexible membrane 124" is not rigid, movement of the optical fluid 140 into the chamber 126" increases the volume of the chamber 126" and changes the shape of the flexible membrane 124". Thus, the power of the lens 110 has been changed. Based on the changes in volume of the reservoir 132B' and chamber 126" and the properties of the flexible membrane 124" and the optical fluid 140, the change in the base power of the lens 110 may be determined. However, because the volume change of the reservoir 132B' is smaller, the change in the base power of the lens 110 is less in FIG. 1D than FIG. 1C.

Both heat sensitive portions 134A and 134B may be heated to at or above the glass transition temperature. Heating may be accomplished using a laser or similar mechanism in the same manner as describe above. FIG. 1E depicts the lens 110 after heating of the heat sensitive portions 134A and 134B. The lens 110 may also have been cooled. The heat sensitive portions 134A' and 134B' have changed shape. As a result, the volumes of the reservoirs 132A' and 132B' have decreased. This forces some of the optical fluid 140 into the chamber 126"'. Because the flexible membrane 124"' is not rigid, movement of the optical fluid 140 into the chamber 126"' increases the volume of the chamber 126"' and changes the shape of the flexible membrane 124"'. Thus, the power of the lens 110 has been changed. Based on the changes in volumes of the reservoirs 132A' and 132B' and chamber 126''' and the properties of the flexible membrane 124''' and the optical fluid 140, the change in the base power of the lens 110 may be determined. Because the volume changes of the reservoirs 132A' and 132B' are larger, the change in the base power of the lens 110 is greater in FIG. 1E than FIGS. 1C and 1D. For example, if the base power of the lens 110 changes by 0.25 diopter for the situation shown in FIG. 1D, then the base power may change by 0.5 diopter for the situation shown in FIG. 1C and by 0.75 diopter for the situation shown in FIG. 1E. Further, the changes shown in FIGS. 1C, 1D and 1E need not occur at the same time. Instead, these changes may be made later based on updated information and/or changes to the patient's eye.

The base power of the lens 110 and thus the IOL 100 may be changed if the lens 110 has the incorrect base power for the patient or the patient's vision changes over time. In some configurations, the power of the lens 110 may be able to be adjusted up or down depending upon whether there is a volume decrease or increase in the reservoir 132A/132B. Because the heat sensitive portions 134A and 134B may be changed via laser, the power of the lens 110 may be changed noninvasively. Thus, the risks of invasive procedures such as changing of the IOL may be avoided. Instead, a simple office visit may be all that is required. Changing the base power of the lens 110 via laser heating may also be more cost effective than changing the entire IOL. In addition, drawbacks of other noninvasive mechanisms for changing the base power of the lens may be avoided. For example, changes need not be locked into the lens 110. Instead, additional heat might be applied at any time throughout the life of the lens 110. Further, the lens 110 does not require special eyewear, such as UV light protective eyewear worn around the clock, around the time the base power is adjusted. In addition, a single office visit may be sufficient to adjust the power of the lens 110. The adjustment may also be quicker. In some cases, the heating, rapid change in shape of the heat sensitive portions 134A/134B, flow of fluid between the reservoir 132A/132B and the chamber 126, the change in volume of the chamber 126 and the attendant change in base power of the lens may take a matter of minutes or less. Thus, the lens 110 may be more easily tuned to the needs of the patients.

FIGS. 2A-2D depict another exemplary embodiment of a heat tunable ophthalmic lens 150 that may be used as or in an IOL. For simplicity, the ophthalmic lens 150 is referred to hereinafter as lens 150. FIGS. 2A-2D depict side views of the ophthalmic lens 110. For clarity, FIGS. 2A-2D are not to scale. The lens 150 may be part of an IOL, such as the IOL 100, that includes the lens 150 and may include haptics (not shown in FIGS. 2A-2E).

The lens 150 has an optic axis 156 as well a lens body 160, a reservoir module 170 and optical fluid 190. The lens body 160, reservoir module 170, optical fluid 190 and optic axis 156 are analogous to the lens body 120, reservoir module 130, optical fluid 140 and optic axis 106, respectively. Thus, the lens body 160, base 162, flexible membrane 164 and chamber 166 are analogous to the lens body 120, base 122, flexible membrane 124 and chamber 126, respectively. Similarly, the reservoir module 170, reservoir 172A/172B and heat sensitive portions 174A and 174B are analogous to the reservoir module 130, reservoir 132A/132B and heat sensitive portions 134A and 134B, respectively. Finally, the optical fluid 190 is analogous to the optical fluid 140. Thus, the structure, function and materials of these components may be analogous to those discussed above. For example, the index of refraction of the optical fluid 190 may match the index of refraction of the lens body 160 to within the tolerances discussed above. Although not shown, the anterior and/or posterior surface may have other features included but not limited to diffraction grating(s). Although indicated as separate components, the reservoir module 170 and the lens body 160 may be integrated together into a single piece.

Also shown is a microfluidic path 180 that connects the reservoir 172A/172B with the chamber 166. The ends of the microfluidic path 180 are shown as dashed lines indicating inlets/outlets to the chamber 166 and reservoir 172A/172B. In some embodiments, the microfluidic path 180 is simply a straight channel. However, in other embodiments, the microfluidic path 180 may have another, more complex structure.

The lens body 170 forms the primary optical component of the lens 150. In contrast, the reservoir module 170 may not be designed to transmit light used in vision. In the embodiment shown, the flexible membrane 164 is pliable and has optical properties that may change in response to an alteration in the volume of the chamber 166. In contrast, the base 162 has stable optical properties and may be relatively fixed in shape. In other embodiments, the base 162 may change shape somewhat in response to changes in the volume of the chamber 166.

The reservoir module 170 is at the periphery of the lens body 160. In some embodiments, the reservoirs 172A and 172B are connected within the reservoir module 170 such that fluid may flow around the periphery of the lens body 160. In other embodiments, the reservoirs 172A and 172B may be disconnected such that any fluid flow between the reservoirs 172A and 172B occurs through the chamber 166 of the lens body 160. The reservoirs 172A and 172B may have different shape(s) in other embodiments.

The heat sensitive portions 174A and 174B of the reservoir module 130 may be part of a single heat sensitive portion. For example, the heat sensitive portions 174A and 174B may be part of a torus that occupies one wall of the reservoir 172A/172B. Alternatively, the heat sensitive portions 174A and 174B may be composed of discrete units. For example, in FIGS. 2A-2D, each heat sensitive portion 174A and 174B includes multiple capsules 175A and 17B, respectively. For simplicity, only one capsule 175A and 175B in each heat sensitive portion 174A and 174B, respectively, is labeled. In some embodiments, each capsule 175A and/or 175B is a single heat sensitive structure that may be thermally isolated from other capsules. In other embodiments, the capsules 175A and 175B are part of a single heat sensitive structure. Selected regions of the heat sensitive portion 174A and 174B may be individually heated to or above their glass transition temperature(s). In the embodiment shown, the capsules 175A and 175B are roughly hemispherical. However, nothing prevents the use of another shape. In the embodiment shown, each of the capsules 175A and 175B has the same size. Thus, each capsules 175A and 175B may contain/displace the same volume of optical fluid 190. In other embodiments the capsules 175A and/or 175B may have different sizes. The volume of optical fluid contained/displaced in each capsule 175A and 175B is still desired to be known and to correspond to a known change in base power. For example, each capsule 175A and 175B may correspond to a base power change of 0.25 diopter, to within desired tolerances. In some cases, this corresponds to a volume for each capsule 175A and 175B of 0.2 mm$^3$. However, other volumes and other base power changes may be used. For example, one capsule 175A might correspond to a 0.25 diopter change, another capsule 175A might correspond to a 0.5 diopter change, and so on. In some embodiments, a change in power of four diopters (e.g. ±2 diopters) may be provided.

Each of the capsules 175A and 175B changes shape in response to the glass transition temperature being reached by the capsule 175A and 175B. After cooling this new shape is stable. Below the glass transition temperature, the shape is substantially fixed as either a capsule or a flat surface. This glass transition temperature of the heat sensitive portions 174A and 174B is desired to be significantly above the normal temperature of the eye and sufficiently low that the heat sensitive portions 174A and 174B may reach the glass transition temperature without damaging the eye. In some embodiments, the capsules 175A and 175B are sufficiently small that localized heating of these capsules 175A and 175B does not adversely affect the eye even though temperatures well above the normal temperature of the eye are reached by the portions 174A and 174B. The capsules 175A and 175B may be formed of the SMP described above and may have the glass transition temperature(s) described above.

Figure 2A:
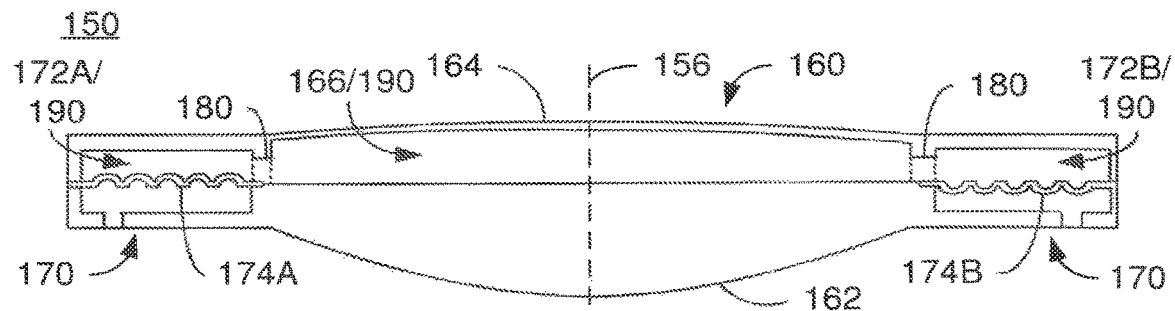
FIGS. 2A-2D depict various views of another exemplary embodiment of a heat tunable ophthalmic device.

As can be seen in FIG. 2A, the orientations of the capsules 175A and 175B with respect to the reservoirs 172A and 172B differ. In particular, each of the capsules 175A displaces a roughly hemispherical volume of optical fluid 190 from the reservoir 172A. Each of the capsules 175B includes a roughly hemispherical volume of optical fluid 190 in the reservoir 172B. As a result, the base power of the lens 150 may be increased or decreased by varying amounts depending upon whether a capsule 175A or a capsule 175B is heated to or above its glass transition temperature and the number of capsules 175A or 175B so heated.

Operation of the lens 150 is discussed with respect to FIGS. 2A-2D. In the ensuing discussion, it is assumed that the lens 150 initially has the configuration shown in FIG. 2A. If the base power of the lens 150 is too high, then the lens 150 is desired to refract light less. This may be accomplished by reducing the curvature of the flexible membrane 164. Because of their orientation with respect to the reservoir 172A, a change in shape of the capsules 175A/heat sensitive portion 174A may be used. More specifically, heat is applied to one or more of the capsules 175A, for example via a laser. The temperature of this capsule 175A is raised to above its glass transition temperature. Consequently, the capsule 175A changes shape.

Figure 2B:
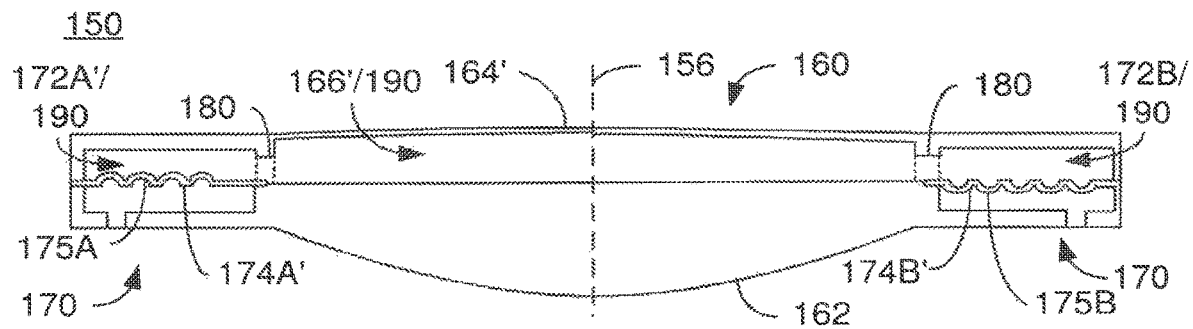

FIG. 2B depicts an exemplary embodiment of the lens 150 after enough heat is applied to the capsule 175A is the closest to the microfluidic path 180 to raise the temperature of the capsule 175A to at or above the glass transition temperature. The lens 150 may subsequently have been cooled to the ambient temperature of the eye. The capsule 175A closest to the chamber 166' has now flattened. This capsule has changed from a first shape (hemispherical) to a second shape (substantially flat). This shape change is stable after cooling. As a result, the reservoir 172A' has increased volume by the approximately the volume of the capsule 175A. The reservoir 172B remains unchanged. Consequently, optical fluid 190 has flowed from the chamber 166' through the microfluidic path 180 to the reservoir 172A'. The pressure from the optical fluid 190 on the flexible membrane 164' is reduced. The flexible membrane 164' flattens and the chamber 166' has a corresponding reduction in volume. The optical power of the lens body 160 is, therefore, reduced. Consequently, the base power of the lens 150 has been noninvasively reduced.

In contrast, suppose the base optical power of the lens 150 is desired to be increased from the situation shown in FIG. 2A. To do so, the curvature of the flexible membrane 164 is desired to be increased. If one or more of the capsules 175B is heat treated to reach a temperature at or exceeding the glass transition temperature, the capsule(s) 175B flattens. Suppose heat is applied to a single capsule 175B, for example via a laser. The temperature of this capsule 175B is raised to above to glass transition temperature of the capsule 175B. Consequently, the capsule 175B changes shape.

Figure 2C:
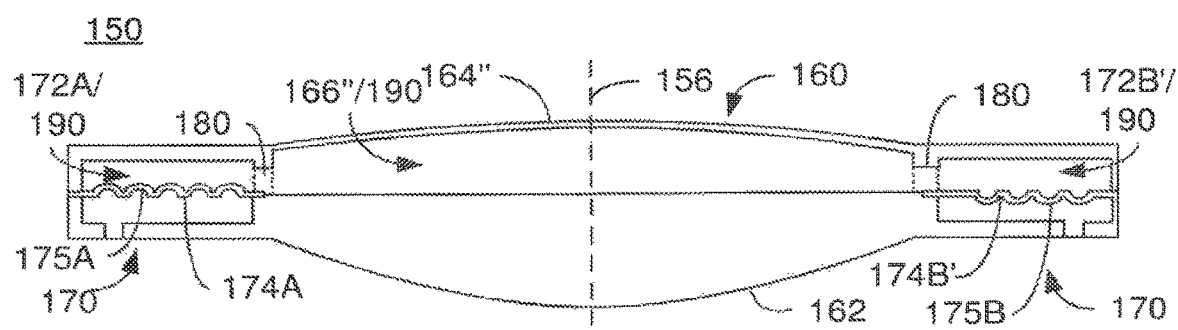

FIG. 2C depicts an exemplary embodiment of the lens 150 after enough heat is applied to the capsule 175B' is the closest to the microfluidic path 180 to raise the temperature of the capsule 175B' to at or above the glass transition temperature. The lens 150 may also have been subsequently cooled to the ambient temperature of the eye. In the heat sensitive portion 174B' of the reservoir module 170, the capsule closest to the chamber 166" has now flattened. This capsule has changed from a hemispherical to substantially flat. As a result, the reservoir 172B' has decreased volume by the approximately the volume of a capsule 175B. The reservoir 172A remains unchanged. Consequently, optical fluid 190 has flowed from the reservoir 172B' through the microfluidic path 180 to the chamber 166". The pressure from the optical fluid 190 on the flexible membrane 164" is increased. The chamber 166" increases in volume and the flexible membrane 164" has a corresponding increase in curvature. The change in volume of the chamber 166" can but need not be equal to the volume of a capsule 175B. The optical power of the lens 110 is, therefore, increased. Consequently, the base power of the lens 150 may be noninvasively enhanced.

Figure 2D:
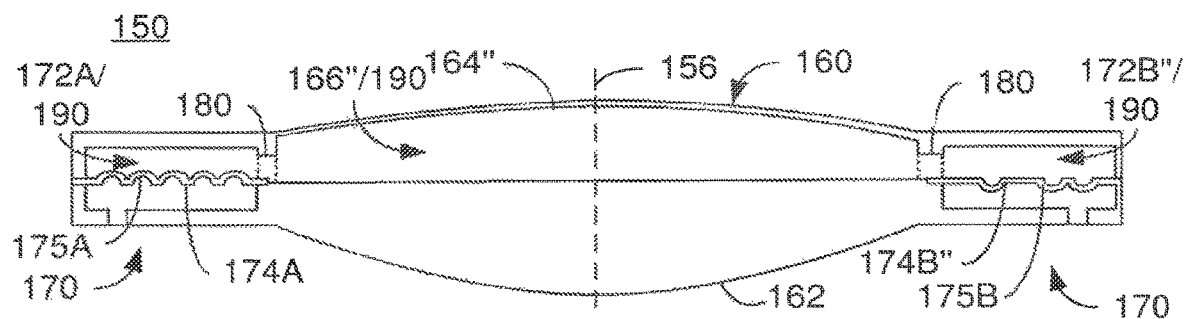

It may be determined that the power of the lens 150 is desired to be further increased. In such a case, more capsule(s) 175B may be heat treated. Such a situation is shown in FIG. 2D. As can be seen from the heat sensitive portion 174B", another capsule 175B has been heat treated and, therefore, is flat. The volume of the reservoir 172B" is further decreased. The optical fluid 190 flows from the reservoir 172B" to the chamber 166". The increase pressure of the optical fluid in the chamber 164" causes further deformation of the flexible membrane 164" and an increase in the volume of the chamber 166". Consequently, the optical power of the lens 150 is further increased. Note that the optical power of the lens 150 may be decreased again by heat treating one or more of the capsules 175A.

The properties of the lens 150 may be noninvasively adjusted. More specifically, the base power of the lens 150 may be noninvasively increased and/or decreased. Thus, benefits analogous to those discussed above for the lens 110 may be achieved.

Figure 3A:
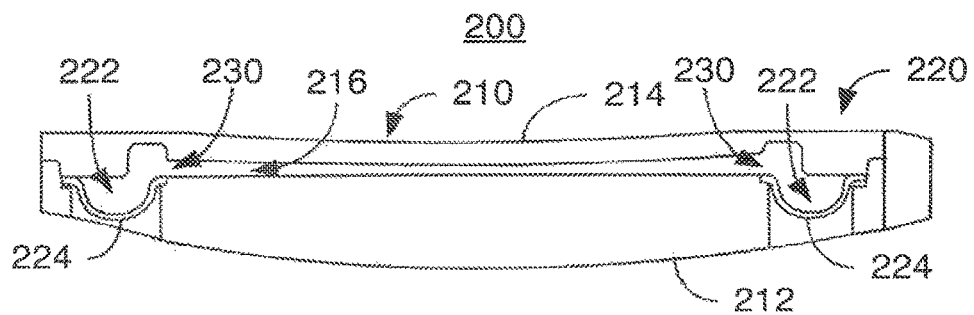
FIGS. 3A-3B depict various views of another exemplary embodiment of a heat tunable ophthalmic lens.
Figure 3B:
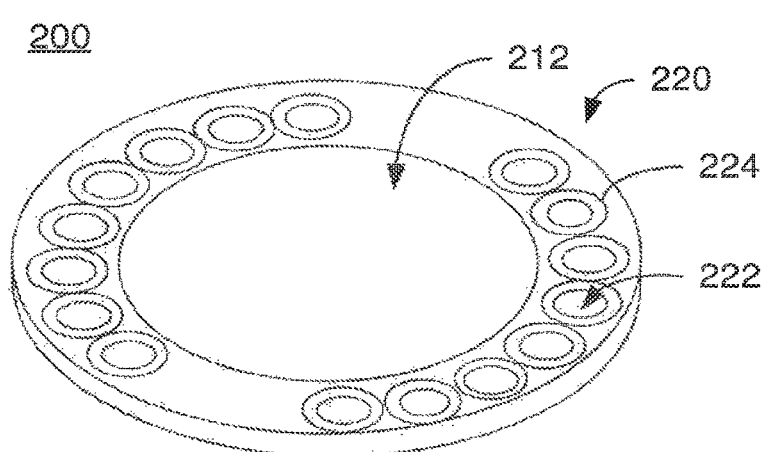

FIGS. 3A-3B depict various views of another exemplary embodiment of a heat tunable ophthalmic lens 200. For simplicity, the ophthalmic lens 200 is referred to hereinafter as lens 200. FIGS. 3A-3B depict side and perspective views of portions of the lens 200. For clarity, FIGS. 3A-3B are not to scale. The lens 200 may be part of an IOL, such as the IOL 100, that includes a lens as well as haptics (not shown in FIGS. 3A-3B). For simplicity, the optic axes are not shown.

The lens 200 has a lens body 210, a reservoir module 220, microfluidic path 230 and optical fluid (not specifically shown in FIGS. 3A-3B). The lens body 210, reservoir module 220, microfluidic path 230 and optical fluid are analogous to the lens body 120/160, reservoir module 130/170, microfluidic path 180 and optical fluid 140/190, respectively. Thus, the lens body 210, base 212, flexible membrane 214 and chamber 216 are analogous to the lens body 120/160, base 122/162, flexible membrane 124/164 and chamber 126/166, respectively. Similarly, the reservoir module 220, reservoir 222 and heat sensitive portions 224 are analogous to the reservoir module 130/170, reservoir 132A/132B/172A/172B and heat sensitive portions 134A/134B/174A/174B, respectively. The structure, function and materials of these components may be analogous to those discussed above. Although not shown, the anterior and/or posterior surface may have other features included but not limited to diffraction grating(s). Although indicated as separate components, the reservoir module 210 and the lens body 220 may be integrated together into a single piece.

In the embodiment shown, the reservoir 222 has walls including individually formed capsules. Each capsule has a heat sensitive portion 224 forming the walls of the capsule. Thus, the heat sensitive portion 224 and capsules 224 are effectively synonymous for the lens 200. The capsules 224 may be a SMP. In the embodiment shown, each capsule 224 is discrete. Each capsule 224 is shown as having the same volume and orientation. In other embodiments, one or more of the capsules 224 might have a different volume and/or a different orientation. For example, eight of the sixteen capsules 224 shown might have an opposite orientation to that shown. Thus, the capsules 224 might have an orientation analogous to the heat sensitive portions 174A and 174B depicted in FIG. 2A. Thus, both increases and decreases in the base power of the lens 200 may be provided.

The lens 200 functions in an analogous manner to the lenses 110 and 150. The lens 200 may, therefore, share the benefits of the lenses 110 and/or 150. In particular, the base power of the lens 200 may be noninvasively tailored to the patient. This may be accomplished by heat treating one or more of the capsules 224, for example via a laser. Consequently, the base power of the lens 200 may be relatively rapidly and easily tuned throughout the life of the lens 200.

Figure 4:
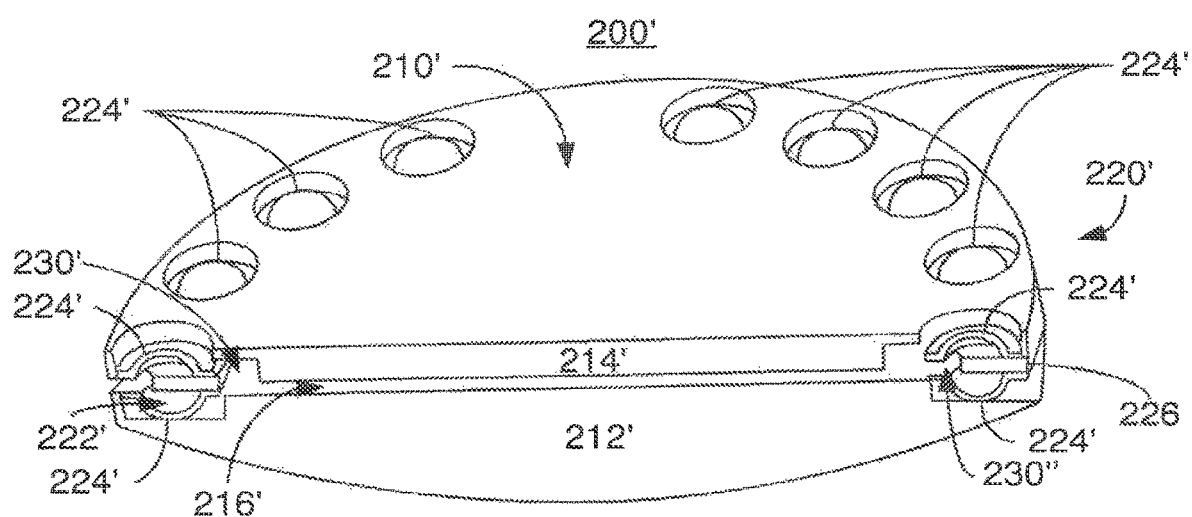
FIG. 4 depicts a perspective cutaway view of another exemplary embodiment of a heat tunable ophthalmic lens.

FIG. 4 depicts a perspective cutaway view of another exemplary embodiment of a heat tunable ophthalmic lens 200'. For simplicity, the ophthalmic lens 200' is referred to hereinafter as lens 200'. For clarity, FIG. 4 is not to scale. The lens 200' may be part of an IOL, such as the IOL 100, that includes a lens as well as haptics (not shown in FIG. 4). For simplicity, the optic axes are not shown.

The lens 200' has a lens body 210', a reservoir module 220' and optical fluid (not specifically shown in FIG. 4). The lens body 210', reservoir module 220', microfluidic path 230' and optical fluid are analogous to the lens body 120/160/210, reservoir module 130/170/220, microfluidic path 180/230 and optical fluid 140/190, respectively. Thus, the lens body 210', base 212', flexible membrane 214' and chamber 216' are analogous to the lens body 120/160/210, base 122/162/212, flexible membrane 124/164/214 and chamber 126/166/216, respectively. Similarly, the reservoir module 220', reservoir 222' and heat sensitive portions 224' are analogous to the reservoir module 130/170/220, reservoir 132A/132B/172A/172B//222 and heat sensitive portions 134A/134B/174A/174B/220, respectively. The structure, function and materials of these components may be analogous to those discussed above. Although not shown, the anterior and/or posterior surface may have other features included but not limited to diffraction grating(s). Although indicated as separate components, the reservoir module 210' and the lens body 220' may be integrated together into a single piece.

In the embodiment shown, the reservoir 222' has walls including individually formed spherical capsules. Thus, the capsules for the lens 200' are spherical instead of hemispherical. Each capsule has a heat sensitive portion 224' forming the walls of the capsule. Thus, the heat sensitive portion 224' and spherical capsules 224' are effectively synonymous for the lens 200. The spherical capsules 224' may be a SMP. In the embodiment shown, each spherical capsule 224' is discrete. Each spherical capsule 224' is shown as having the same volume. In other embodiments, one or more of the capsules 224' might have a different volume. In the embodiment shown, the upper and lower hemispherical heat sensitive portions 224' of the spherical capsules may be individual heat treated.

The lens 200' functions in an analogous manner to the lenses 110, 150 and 200. The lens 200' may, therefore, share the benefits of the lenses 110, 150 and/or 200. In particular, the base power of the lens 200' may be noninvasively tailored to the patient. This may be accomplished by heat treating one or more of the capsules 224', for example via a laser. Consequently, the base power of the lens 200' may be relatively rapidly and easily tuned throughout the life of the lens 200'.

Figure 5:
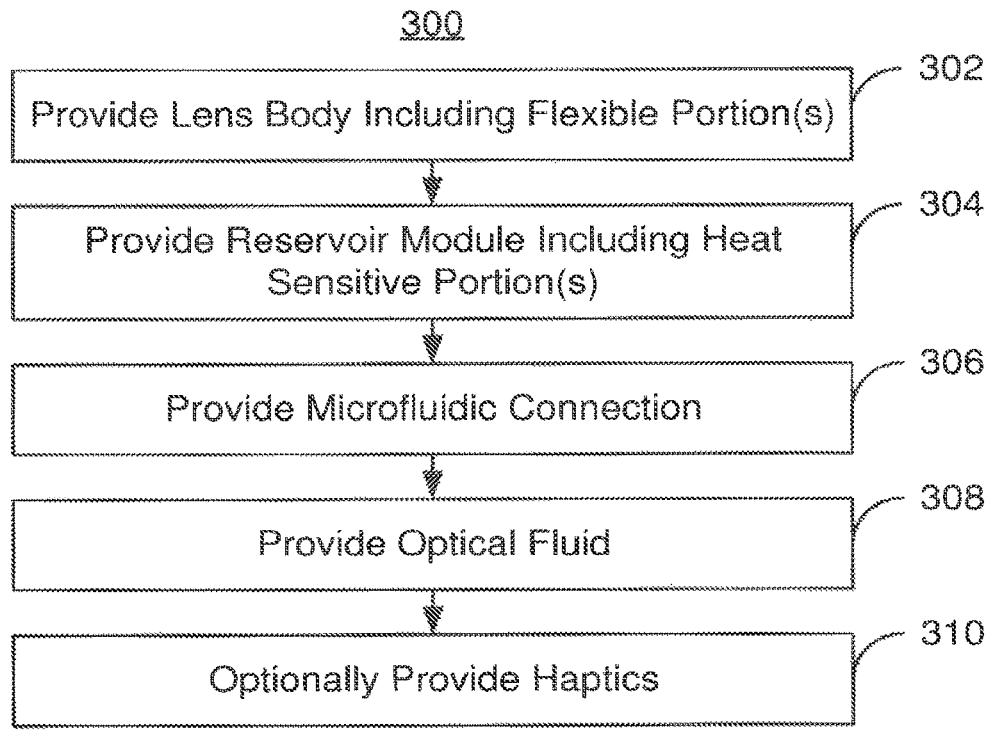
FIG. 5 is a flow chart depicting an exemplary embodiment of a method for providing a heat tunable ophthalmic device.

FIG. 5 is a flow chart depicting an exemplary embodiment of a method 300 for providing an ophthalmic lens. For simplicity, some steps may be omitted, interleaved, and/or combined. The method 300 is also described in the context of the ophthalmic device 100 and ophthalmic lens 110. However, the method 300 may be used with one or more of ophthalmic lenses 110, 150, 200, 200' and/or an analogous ophthalmic device.

The lens body 120 is provided, via step 302. Step 302 includes providing the base 122, flexible membrane 124 and cavity 126. Some or all of the microfluidic path, such as a microfluidic path 180 or 230, may be provided as part of shaping the lens body 120. Step 302 may include forming and/or connecting the base 122 and flexible membrane 124 such that the empty space for the chamber 126 resides between them. Step 302 may also include forming any diffraction gratings on the flexible membrane 124 and/or base 122.

The reservoir module 130 is provided, via step 304. Step 304 may include providing the heat sensitive portions 134A and 134 at the border of the reservoir 132A/132B. For example, the desired SMP, having the appropriate shape, size, glass transition temperature and absorption of laser light is provided. Step 304 may also include forming some or all of the microfluidic path.

If not already completed in steps 302 and 304, the microfluidic path 180 or 230 is provided, via step 306. Step 306 may simply include providing an aperture or channel between the chamber 126 and the reservoir 132A/132B. Alternatively, a more complex path may be formed.

The optical fluid 140 is provided in the lens 110, via step 308. Step 308 may include filling the lens 110 with the desired optical fluid 140 and sealing the lens 110. Thus, the optical fluid 140 may flow between the chamber 126 and the reservoir 132A/132B. The haptics 102 and 104 may optionally be provided, via step 310.

Using the method 300, the IOL 100 and ophthalmic lens(es) 110, 150, 200 and/or 200' may be provided. Thus, the benefits of one or more of the lenses 110, 150, 200 and/or 200' may be attained.

Figure 6:
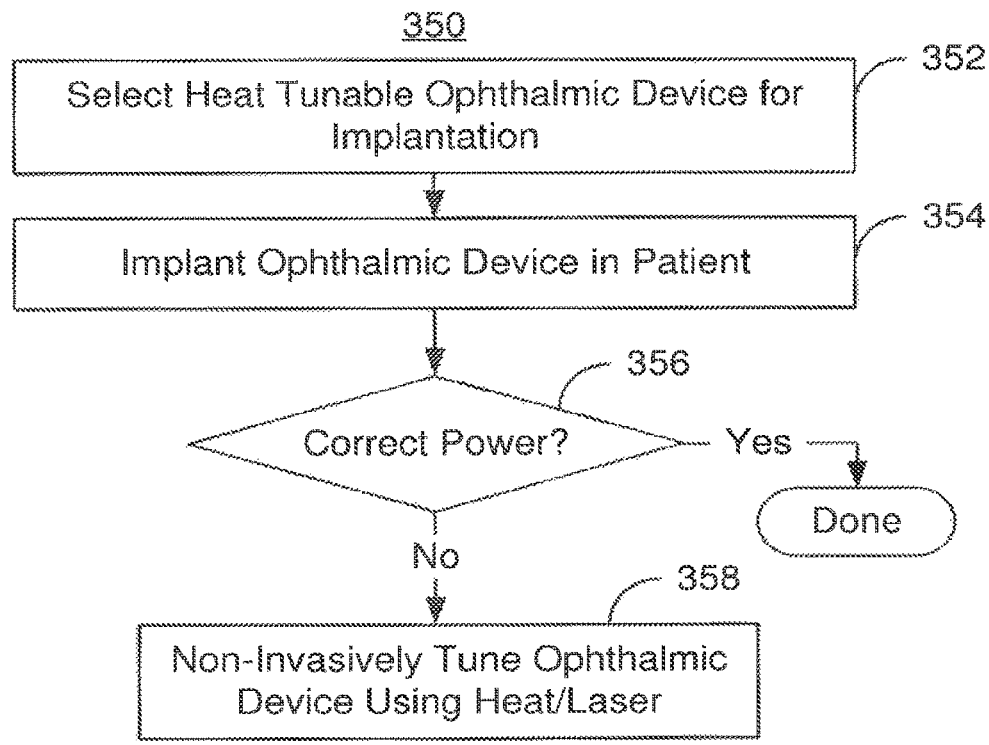
FIG. 6 is a flow chart depicting an exemplary embodiment of a method for using a heat tunable ophthalmic device.

FIG. 6 is a flow chart depicting an exemplary embodiment of a method 350 for treating an ophthalmic condition in a patient and tuning the lens. For simplicity, some steps may be omitted, interleaved, and/or combined. The method 350 is also described in the context of using the IOL 100 and lens 110. However, the method 350 may be used with one or more of lenses 150, 200 and/or 200'.

An IOL 100 that is heat tunable is selected for implantation in an eye of the patient, via step 352. The IOL 100 includes a lens body 120, a reservoir module 130, a fluidic connection between the chamber 126 and the reservoir 132A/132B and optical fluid 140. Part of the selection process may involve determining the correction needed for the patient's eyesight and selecting the IOL 100 having the appropriate power.

The IOL 100 is implanted in the patient's eye, via step 354. Step 354 may include replacing the patient's own lens with the IOL 100 or augmenting the patient's lens with the IOL 100.

It is determined whether the IOL 100 that was implanted has the correct base power, via step 150. Step 150 may include re-measuring the patient's vision. This step may take place shortly after implantation or at a remote time. This is because the IOL 100 may be tuned throughout its lifetime in some embodiments. If the base power is correct, then the method terminates.

However, if the base power is not correct, then the base power of the IOL 100 may be noninvasively tuned, via step 358. If increases or decreases in the base power are desired to be corrected, then a lens analogous to the lens 150 may be selected in step 352. Step 358 may include locating the desired regions of the heat sensitive portion 134A and/or 134B to be heated. A laser may then be aimed at the desired portions of the heat sensitive portions 134A and/or 134B and fired until the glass transition temperature has been reached or exceeded. In some embodiments, a low duty cycle may be used for the laser to reduce heating of the eye. Step 358 may be carried out during a single out-patient visit. In addition, steps 356 and 358 may be iteratively repeated until the desired power of the lens 110 is reached. Further, steps 356 and 358 may be repeated at various times throughout the life of the lens 110.

Using the method 350, a physician may be able to more quickly and easily tune the base power of the IOL 100 using heat. This may be achieved without requiring additional eyewear for the patient or locking the changes in for the IOL 100. Consequently, the burden on both the physician and patient may be diminished. The method 350 may also be safer for the patient because the method 350 may be performed non-invasively. Consequently, the benefits of the heat tunable IOL 100 and lenses 110, 150, 200 and/or 200' may be achieved.

A method and system for providing a heat tunable IOL have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. An intraocular lens, comprising:
a lens body having a chamber therein, at least a portion of the lens body being flexible, the lens body having a lens body index of refraction;
a reservoir region fluidly coupled with the chamber of the lens body and positioned at least partially circumferentially around the chamber of the lens body, the reservoir region comprising a plurality of heat sensitive structures that change shape in response to absorbing light energy from a laser; and
an optical fluid residing in the chamber and the reservoir region, the optical fluid having an optical fluid index of refraction, wherein the optical fluid is adapted to move between the reservoir region and the chamber in order to cause a base power change of the intraocular lens;
wherein a first portion of the plurality of heat sensitive structures is configured to absorb light energy to change shape to drive a first volume of optical fluid from the reservoir region to the chamber, wherein the first volume of optical fluid corresponds to a base power change of not more than 0.25 diopter; and
wherein a second portion of the plurality of heat sensitive structures is configured to absorb light energy to change shape to drive optical fluid from the chamber to the reservoir region.

2. The intraocular lens of claim 1, wherein the second portion of the plurality of heat sensitive structures is further configured to drive a second volume of optical fluid from the chamber to the reservoir region.

3. The intraocular lens of claim 2, wherein the first volume of optical fluid and the second volume of optical fluid are the same.

4. The intraocular lens of claim 2, wherein the first volume of optical fluid and the second volume of optical fluid are different.

5. The intraocular lens of claim 1, wherein each heat sensitive structure of the first portion of the plurality of heat sensitive structures is further configured to drive a predetermined volume of optical fluid from the reservoir region to the chamber.

6. The intraocular lens of claim 5, wherein each of the predetermined volumes are the same.

7. The intraocular lens of claim 5, wherein each of the predetermined volumes is equal to either a primary volume or a secondary volume.

8. The intraocular lens of claim 1, wherein the plurality of heat sensitive structures are configured to change shape in response to reaching a temperature of at least forty-five degrees Celsius.

9. The intraocular lens of claim 8, wherein the temperature is at least sixty degrees Celsius and not more than one hundred degrees Celsius.

10. The intraocular lens of claim 1, wherein the at least the portion of the lens body includes a flexible membrane.

11. The intraocular lens of claim 1, wherein at least a portion of each of the plurality of heat sensitive structures comprises a shape memory polymer having a glass transition not less than a threshold temperature.

12. The intraocular lens of claim 11, wherein the shape memory polymer comprises an additive that absorbs light energy in a selected wavelength range.

* * * * *